United States Patent [19]  [11] 4,248,239
Ricciardelli  [45] Feb. 3, 1981

[54] MEDICAL SENSOR ASSEMBLY WITH BATTERY

[75] Inventor: Robert H. Ricciardelli, Waukesha, Wis.

[73] Assignee: Biochem International Inc., Wauwatosa, Wis.

[21] Appl. No.: 42,914

[22] Filed: May 29, 1979

[51] Int. Cl.³ .............................................. A61B 5/05
[52] U.S. Cl. .................................................. 128/635
[58] Field of Search ..................... 128/635; 204/195 B

[56] References Cited
U.S. PATENT DOCUMENTS

| 3,340,866 | 9/1967 | Nöller .............................. 128/635 X |
| 3,399,667 | 9/1968 | Nishimoto et al. ............... 128/635 X |

*Primary Examiner*—Kyle L. Howell
*Attorney, Agent, or Firm*—Hume, Clement, Brinks, Willian & Olds

[57] ABSTRACT

A polarized sensor assembly for a polarographic oxygen sensor. The assembly comprises a sensor head and a shielded cable, with a power unit in the cable. The head electrodes remain polarized at all times, permitting transfer of the sensor assembly from one patient monitoring system amplifier to another without losing its polarization.

3 Claims, 4 Drawing Figures

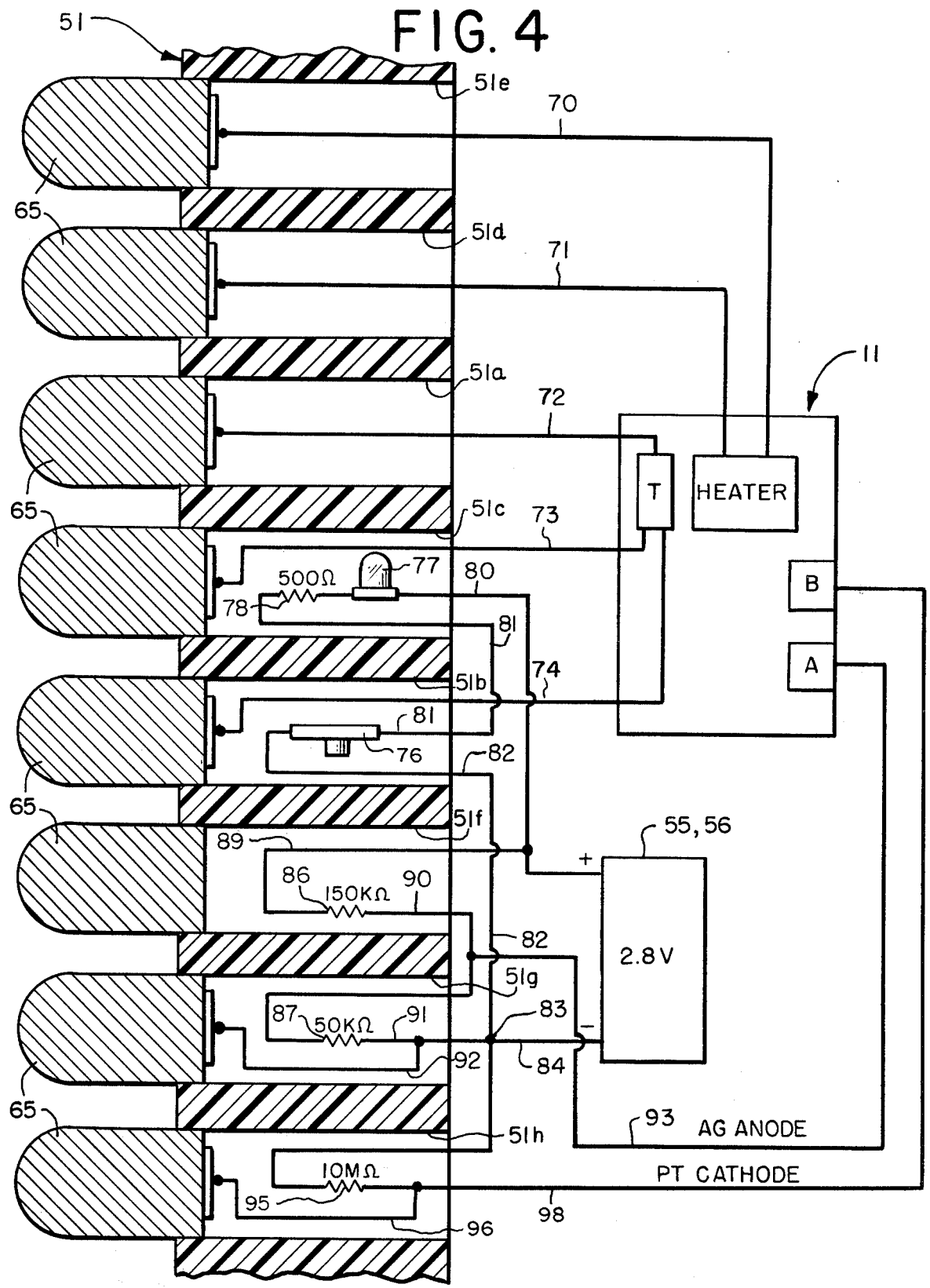

MEDICAL SENSOR ASSEMBLY WITH BATTERY

FIELD OF THE INVENTION

This invention is generally in the field of medical technology as it relates to monitoring a patient's oxygen level. It relates particularly to a polarographic oxygen sensor for monitoring a patient's oxygen level.

BACKGROUND OF THE INVENTION

Polarographic oxygen sensors are well-known in medical technology. In operation, such a sensor determines the transfer rate of oxygen through a diffusion barrier by measuring the related limiting reduction current at a polarized electrode. A monitoring system would conventionally include a sensor head having an anode and a cathode exposed to an electrochemically active surface. The sensor head has a lead cable extending from it and adapted to be connected to an amplifier in the system. Current supplied from the amplifier normally maintains the electrode in a polarized state.

The sensor head and cable are readily detachable from the amplifier. In normal operation they might be used on patient monitoring for a period of time and then detached from the monitoring system amplifier for use on another patient in another system. They might also be stored temporarily. In any case, detaching the sensor head and cable from the system causes the head to become depolarized and, prior to its reuse, it must be repolarized. Repolarization requires up to two hours as a result of which the sensor can't be used again immediately.

SUMMARY OF THE INVENTION

An object of the present invention is to provide an improved sensor assembly for a monitoring system.

Still another object is to provide an improved polarized sensor assembly of the aforedescribed character which does not become depolarized when detached from the system amplifier.

Another object is to provide a new and improved power unit for a patient oxygen monitoring system.

The foregoing and other objects are realized in accord with the present invention by providing a sensor assembly incorporating a power unit for maintaining polarization of the electrodes in the sensor head. The sensor assembly comprises a sensor head and a shielded cable permanently affixed to the head with a quick disconnect connector at its free end for attaching the assembly to the amplifier of a monitoring system.

The cable contains a power unit. The power unit includes two mercury or similar dry cells which produce one and four-tenths (1 4/10) volts each. The batteries are connected to the anode and cathode of the sensor head through a voltage divider and test circuit in the battery unit.

The power unit includes a phenolic cylinder having an aluminum housing surrounding one end of it. The phenolic cylinder contains eight longitudinally extending, parallel passages formed through it, seven of them around the periphery of the cylinder and one on the center line of the cylinder. One end of the cylinder faces a battery chamber. The other end of the cylinder seats in the aluminum housing which includes a shield extending beyond the cylinder. The shield surrounds connector pins seated in corresponding passages and extending therefrom for quick disconnect, in a conventional manner, to the amplifier.

Three of the pins are connected to leads which extend through three cylinder passages to, and through, a battery compartment and, from there, through the shielded cable to a conventional thermistor in the sensor head. These three cylinder passages include the center line passage and two of the peripherally arranged passages.

Two of the pins are connected to leads which extend through two other cylinder passages to, and through, the battery compartment and, from there, through the shielded cable to a heater in the sensor head. These passages are adjacent to the peripherally arranged thermistor lead passages. The three remaining pins include a conventional shield pin and two dummies. They are present in a standard Burndy connector which includes the basic phenolic cylinder and the aluminum housing.

The battery chamber contains the two dry cells. They are connectd in series in a circuit which includes resistors in the cylinder passages. The circuit extends to and includes the sensor head electrodes.

From the battery negative terminal a lead extends to a spring-loaded test switch in the phenolic cylinder. A lead from the test switch extends to a five hundred (500) ohm resistor, from there to a light emitting diode in the cylinder, and finally to the battery positive terminal. The result of this arrangement is that when the test switch is pressed the light goes on if the battery has a sufficient charge; i.e., in excess of two (2) volts, for example.

There are three other resistors disposed in the cylinder passages. Two of these, a one hundred and fifty (150) kilo-ohm resistor, and a fifty (50) kilo-ohm resistor, function as a voltage divider. The battery positive terminal is connected by a lead through the former resistor, to the latter resistor, and from there back to the battery negative terminal. A lead is tapped off between the one hundred and fifty (150) kilo-ohm resistor and the fifty (50) kilo-ohm resistor after the voltage drop through the former. This lead is connected through the battery cable to the anode.

Battery negative is connected by a lead to a ten (10) mega-ohm resistor. This resistor is, in turn, connected by a lead to the cathode. It has a "dropping" function which permits current to flow between the anode and the cathode.

BRIEF DESCRIPTION OF THE DRAWINGS

The invention, including its construction and method of operation, together with additional objects and advantages thereof, is illustrated more or less diagrammatically in the drawings, in which:

FIG. 4 is a diagrammatic view of the electrical circuitry for the sensor assembly, shown in an exploded illustration of the circuits mounting cylinder chassis.

DESCRIPTION OF THE PREFERRED EMBODIMENT

Figure 1:
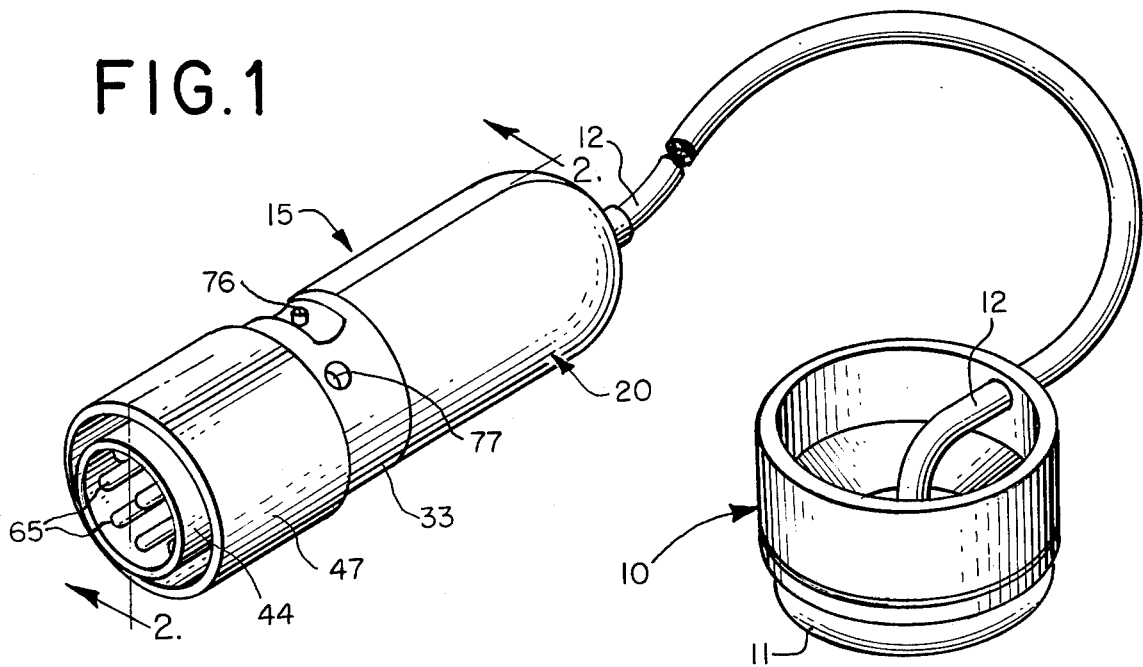
FIG. 1 is a perspective view of a sensor assembly embodying features of the present invention.

Referring now to the drawings, and particularly to FIG. 1, a sensor assembly embodying features of the invention is illustrated generally at 10. The sensor assembly 10 includes a sensor head 11 and a cable 12 for connecting the sensor assembly 10 to the amplifier (not shown) in a conventional monitor unit.

According to the invention, the sensor assembly 10 includes a battery unit 15 in the cable 12. The battery unit 15 provides a polarization bias to electrodes in the sensor head 11 whether the cable 12 is connected to the amplifier or not.

Figure 2:
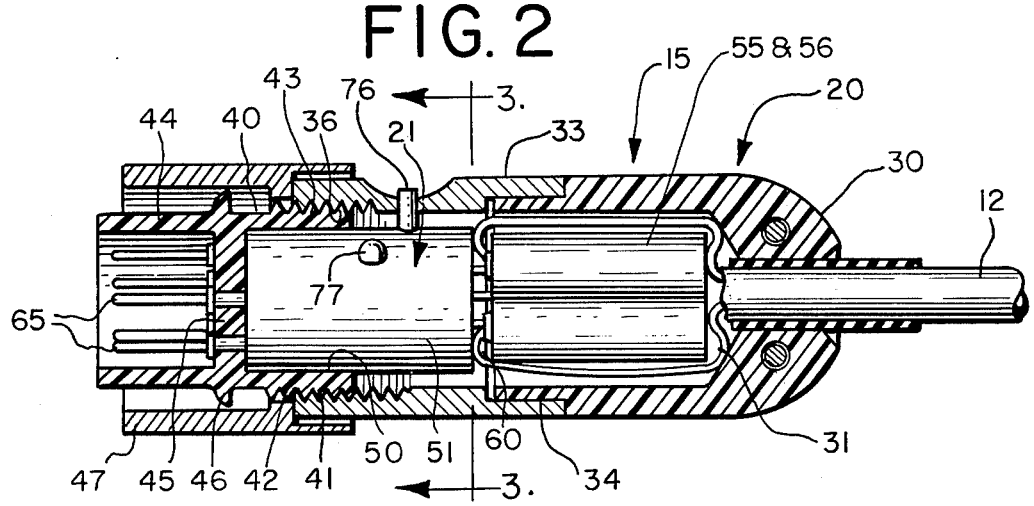
FIG. 2 is an enlarged view, partially in section, of the battery unit component in the sensor assembly illustrated in FIG. 1.
Figure 3:
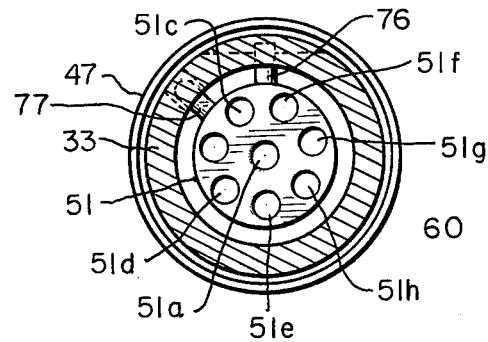
FIG. 3 is a sectional view taken along line 3—3 of FIG. 2.

Referring now to FIGS. 2 and 3, the battery unit 15 includes a housing 20 enclosing the battery circuit and connector subassembly 21. The battery circuit and connector sub-assembly 21 is connected to the sensor head through the cable 12. The subassembly 21 is adapted to be connected to an amplifier (not shown) in a manner which will hereinafter be discussed.

The housing 20 includes a cap member 30 molded of plastic or the like and having a battery compartment 31 therein. The cap member 30 is joined through an interference fit with a cylindrical middle member 33, the joinder being made at 34. The member 33 is machined from stainless steel and is internally threaded at its outer end at 36. A conventional Burndy sleeve connector 40, externally threaded at its inner end 41, is threaded into the middle member 33 in the manner illustrated in FIG. 2.

The sleeve connector 40 includes an inner sleeve 42 fabricated of Aluminum and having an inner section 43 and an outer section 44. The inner section 43 and the outer section 44 are separated by a wall 45 which is perforated in a manner hereinafter discussed. Surrounding the wall 45 is an annular shoulder 46 which, when the sleeve connector 40 is threaded in place, serves to retain a conventional one-quarter turn sleeve nut 47 on the battery unit 15.

The inner section 43 defines a socket 50 in which a phenolic cylinder 51 is mounted. The phenolic cylinder 51 extends toward the battery compartment 31 in the cap member 30. A pair of one point four (1.4) volt mercury dry cell batteries 55 and 56 are mounted in the battery compartment 31. A sensor assembly circuit 60 includes the batteries 55 and 56 and extends into the phenolic cylinder 51 in a manner hereinafter discussed.

Referring particularly to FIG. 3 the phenolic cylinder 51 and portions of the sensor assembly circuit 60 are shown in cross-section to illustrate the cylinder internal configuration and the placement of various components in the assembly circuit. There it will be seen that the phenolic cylinder 51 has eight passages 51a–51h formed therein. The eight passages extend parallel to each other and to the axis of the cylinder 51, with the passage 51a formed on the axis and the remaining seven passages formed in evenly spaced relationship around the periphery of the cylinder.

It will be recalled that the aforedescribed sleeve connector member has a wall 45 which separates an inner section 43 and an outer section 44. This wall 45 was described as having appertures therein and it is through these appertures that eight connector pins 65 extend into communication with each of the passages 51a–51h in the phenolic cylinder 51. The pins 65 provide terminals for the sensor assembly circuit 60 in a manner hereinafter discussed.

The sensor assembly circuit 60 is best illustrated in FIG. 4, where the phenolic cylinder 51 and the passages 51a–51h are illustrated in "rolled-out"; i.e., planar relationship. A connector pin 65 is illustrated extending into each of the passages 51a–51h.

The sensor assembly circuit 16 includes a lead 70 extending from the pin 65 in the passage 51e, through this passage and the cable 12, to the heater H in the sensor head 11. Another lead 71 extends from a pin 65 in the passage 51d, through that passage and the cable 12, to the heater H also.

Three leads 72, 73, and 74 extend from corresponding pins 65 through passages 51a, 51c, and 51d, respectively, and then through the cable 12, to a conventional thermistor in the head 11. As will be seen, the leads 73 and 74 occupy the passages 51c and 51b with other components of the circuit 60. These components permit testing of the circuit 60.

Extending radially through the passage 51b from the outside of the phenolic cylinder 51, in the manner illustrated in FIG. 3, is a spring loaded push button switch 76 of conventional construction. Extending radially into the passage 51c, from the outside of the phenolic cylinder 51, in the manner also illustrated in FIG. 3, is a test signal light 77. The passage 51c also has a conventional five hundred (500) ohm resistor 78 mounted therein.

A lead 80 from the positive terminal of the two cell battery sub-assembly 55, 56 in the battery compartment 31 connects the positive terminal to the test signal light 77. A lead 81 having the resistor 78 interposed therein extends from the light 77 out of the passage 51c and into the passage 51b where it is connected to the switch 76. The switch 76 is, in turn, connected by a lead 82 to a junction 83 with a lead 84 to the negative terminal of the battery subassembly 55, 56. The result of this arrangement is that when the test switch 76 is pressed the light 77 goes on if the battery has a sufficient charge; i.e., in excess of two volts in the present illustration.

FIG. 2 illustrates the switch push button 85 extending radially outward through an aperture in the housing middle member 33. It can be pressed easily by the operator in this location. The light 77 protrudes radially through another aperture (not shown) in the member 33.

Mounted in the passge 51f is a one hundred and fifty (150) kilo ohm resistor 86. Mounted in the adjoining passage 51g is a 50 kilo ohm resistor 87. These two resistors function as a voltage divider. The battery positive terminal is connected by a lead 89 to the resistor 86. A lead 90 connects the resistor 86 to the resistor 87. Lead 91 then connects the resistor 87 back to the junction 83 and, accordingly, with battery negative. A lead 92 connects corresponding pin 65 to the lead 91.

A lead 93 is tapped off between the one hundred and fifty (150) kilo ohm resistor 86 and the 50 kilo ohm resistor 87, in the lead 90. This lead 93 is connected through the battery cable 12 to the anode A in the sensor head 11. The tap-off of the lead 93 is thus made after a voltage drop from battery positive through the one hundred and fifty (150) kilo ohm resistor 86.

Finally, the passage 51h has a ten (10) mega ohm resistor 95 mounted therein. The ten (10) mega ohm resistor is connected by a lead 96 from the junction 83, and thus from the negative terminal of the battery sub-assembly 55, 56. The resistor 95 is, in turn, connected by a lead 98 through the cable 12 to the cathode B in the sensor head 11. The resistor 95 has a "dropping" function which permits current to flow between the anode A and the cathode B. A lead 96 connects corresponding pin 65 to the lead 98.

The sensor assembly 10 permits more efficient system utilization. By eliminating polarization delays it lowers effective cost. The battery unit construction is simple and compact while being highly functional. Testing can be done coincident with cable handing and assembly 10 attachment.

While several embodiments described herein are at present considered to be preferred, it is understood that various modifications and improvements may be made therein, and it is intended to cover in the appended claims all such modification and improvements as fall within the true spirit and scope of the invention.

What is desired to be claimed and secured by Letters Patent of the United States is:

1. A medical sensor assembly for monitoring a patient's system by sensing skin surface conditions, comprising:
   a. a sensing head for securing to a patient's skin surface having an anode and a cathode therein,
   b. a shielded cable extending from said head for releasably connecting said sensor assembly to a monitor system component, and
   c. battery means in one of said head and said cable for maintaining a voltage bias across said anode and cathode whether said cable is connected to or disconnected from said monitor component.

2. The medical sensor assembly of claim 1, further characterized in that:
   a. said battery means is disposed in said cable.

3. The medical sensor assembly of claim 2 further characterized by and including:
   a. a connector assembly in said cable for releasably connecting said sensor assembly to a monitor system component,
   b. said connector assembly including said battery means, and
   c. lead means extending from terminal pins in said connector assembly through said cable to said sensing head.

* * * * *